(12) United States Patent
Nishio et al.

(10) Patent No.: US 10,610,083 B2
(45) Date of Patent: Apr. 7, 2020

(54) OBSERVATION APPARATUS AND ENDOSCOPE SYSTEM

(71) Applicant: OLYMPUS CORPORATION, Tokyo (JP)

(72) Inventors: Masahiro Nishio, Hachioji (JP); Takeshi Ito, Hino (JP); Satoshi Ohara, Hachioji (JP); Motoki Tabata, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 35 days.

(21) Appl. No.: 15/585,269

(22) Filed: May 3, 2017

(65) Prior Publication Data

US 2017/0231472 A1 Aug. 17, 2017

Related U.S. Application Data

(63) Continuation of application No. PCT/JP2014/079453, filed on Nov. 6, 2014.

(51) Int. Cl.
*A61B 1/00* (2006.01)
*H04N 5/232* (2006.01)
(Continued)

(52) U.S. Cl.
CPC ...... *A61B 1/00036* (2013.01); *A61B 1/00009* (2013.01); *A61B 1/00045* (2013.01);
(Continued)

(58) Field of Classification Search
None
See application file for complete search history.

(56) References Cited

U.S. PATENT DOCUMENTS

| | | | |
|---|---|---|---|
| 2007/0066868 A1* | 3/2007 | Shikii | A61B 1/00036 600/118 |
| 2008/0262299 A1* | 10/2008 | Niida | A61B 1/05 600/110 |

(Continued)

FOREIGN PATENT DOCUMENTS

| | | | |
|---|---|---|---|
| JP | 2000-147389 A | | 5/2000 |
| JP | 2000147389 A | * | 5/2000 |

(Continued)

OTHER PUBLICATIONS

Japanese Office Action dated Jan. 23, 2018 in Japanese Patent Application No. 2016-557400.
(Continued)

*Primary Examiner* — James M Pontius
*Assistant Examiner* — Tyler B Edwards
(74) *Attorney, Agent, or Firm* — Scully, Scott, Murphy & Presser, P.C.

(57) ABSTRACT

A light source illumination unit has operation modes including at least a normal electric power mode to operate with first electric power consumption, and a low electric power mode to operate with second electric power consumption lower than the first electric power consumption. A controller selects at least one of the operation modes in accordance with the current usage, and controls the light source illumination unit in accordance with the selected operation mode.

20 Claims, 10 Drawing Sheets

(51) Int. Cl.
*G02B 23/24* (2006.01)
*H04N 5/225* (2006.01)
*A61B 1/06* (2006.01)
*A61B 1/04* (2006.01)
*H04N 5/235* (2006.01)

(52) U.S. Cl.
CPC .............. *A61B 1/04* (2013.01); *A61B 1/06* (2013.01); *A61B 1/0676* (2013.01); *G02B 23/2469* (2013.01); *G02B 23/2484* (2013.01); *H04N 5/2256* (2013.01); *H04N 5/2354* (2013.01); *H04N 5/23241* (2013.01); *H04N 2005/2255* (2013.01)

(56) References Cited

U.S. PATENT DOCUMENTS

2013/0296651 A1* 11/2013 Ito .......................... A61B 1/06 600/109
2015/0335232 A1* 11/2015 Ito .......................... G02B 23/26 362/13

FOREIGN PATENT DOCUMENTS

| | | | |
|---|---|---|---|
| JP | 2005-237430 A | | 9/2005 |
| JP | 2005237430 A | * | 9/2005 |
| JP | 2007-082664 A | | 4/2007 |
| JP | 2008-264252 A | | 11/2008 |
| JP | 2012-095911 A | | 5/2012 |
| JP | 2012-152273 A | | 8/2012 |
| JP | 2014-150932 A | | 8/2014 |

OTHER PUBLICATIONS

International Search Report dated Feb. 17, 2015 issued in PCT/JP2014/079453.
Chinese Office Action dated Mar. 5, 2018 in Chinese Patent Application No. 201480083203.X.
English translation of International Preliminary Report on Patentability dated May 18, 2017 together with the Written Opinion received in related International Application No. PCT/JP2014/079453.

* cited by examiner

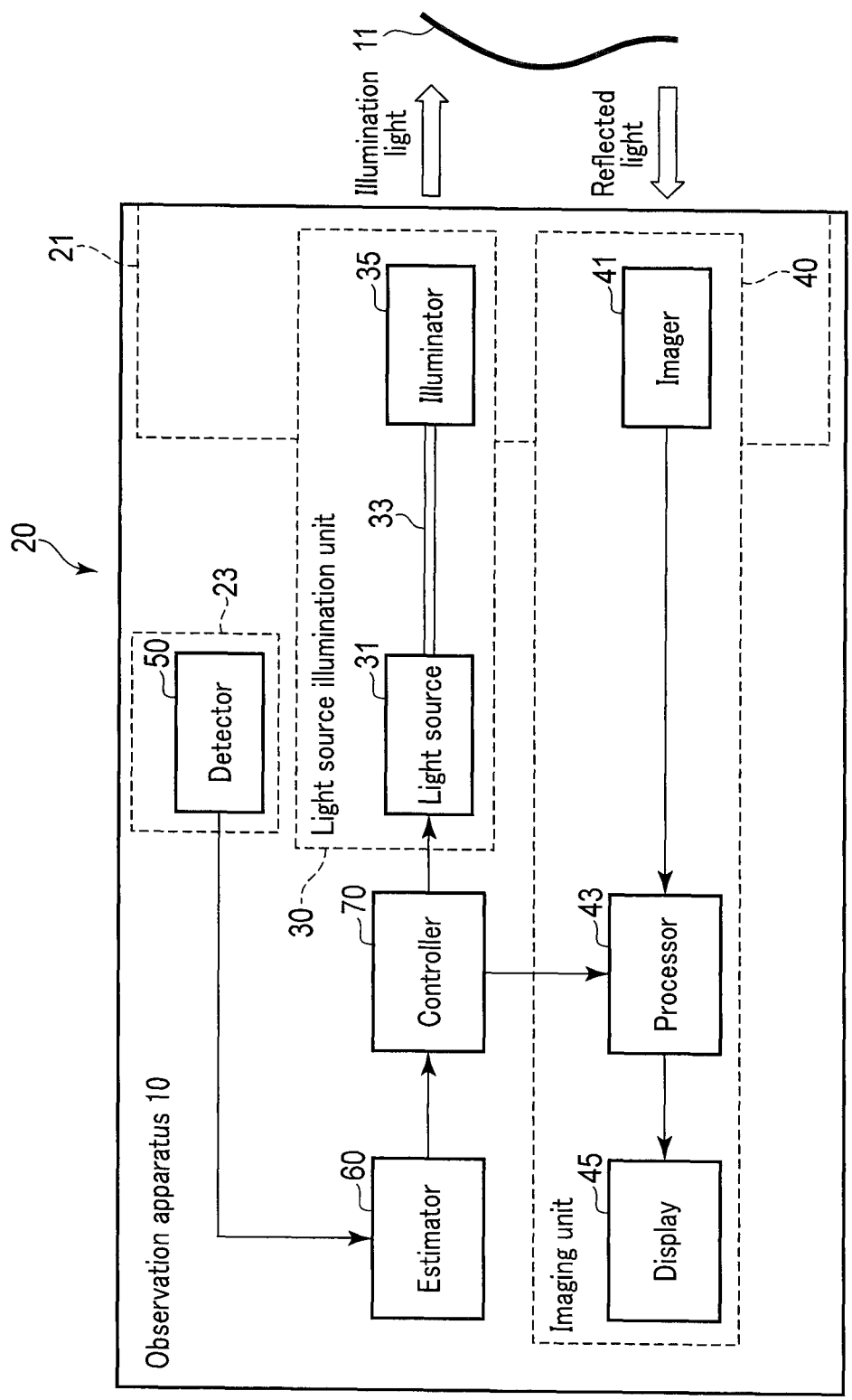
F I G. 2A

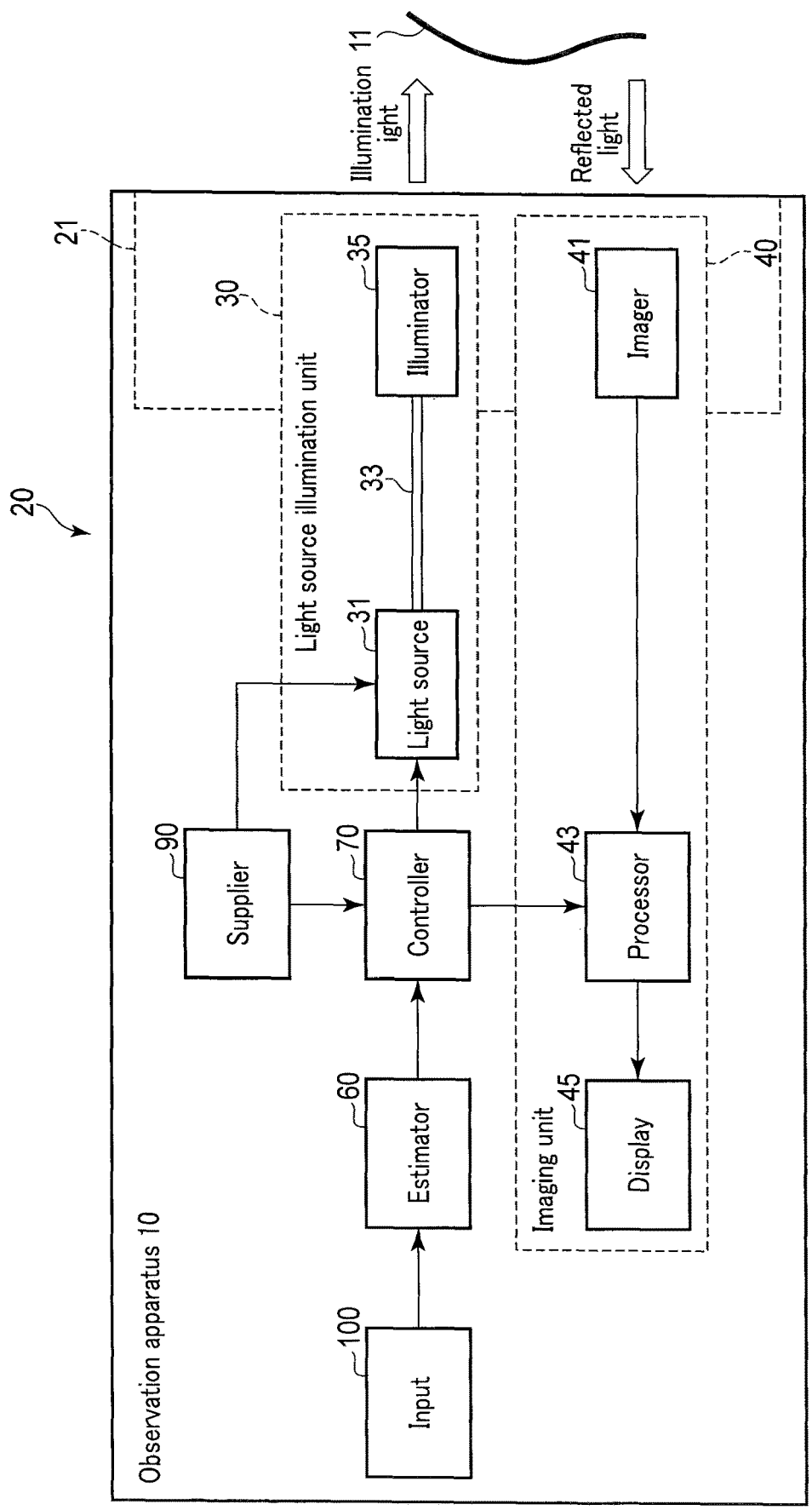
F I G. 3A

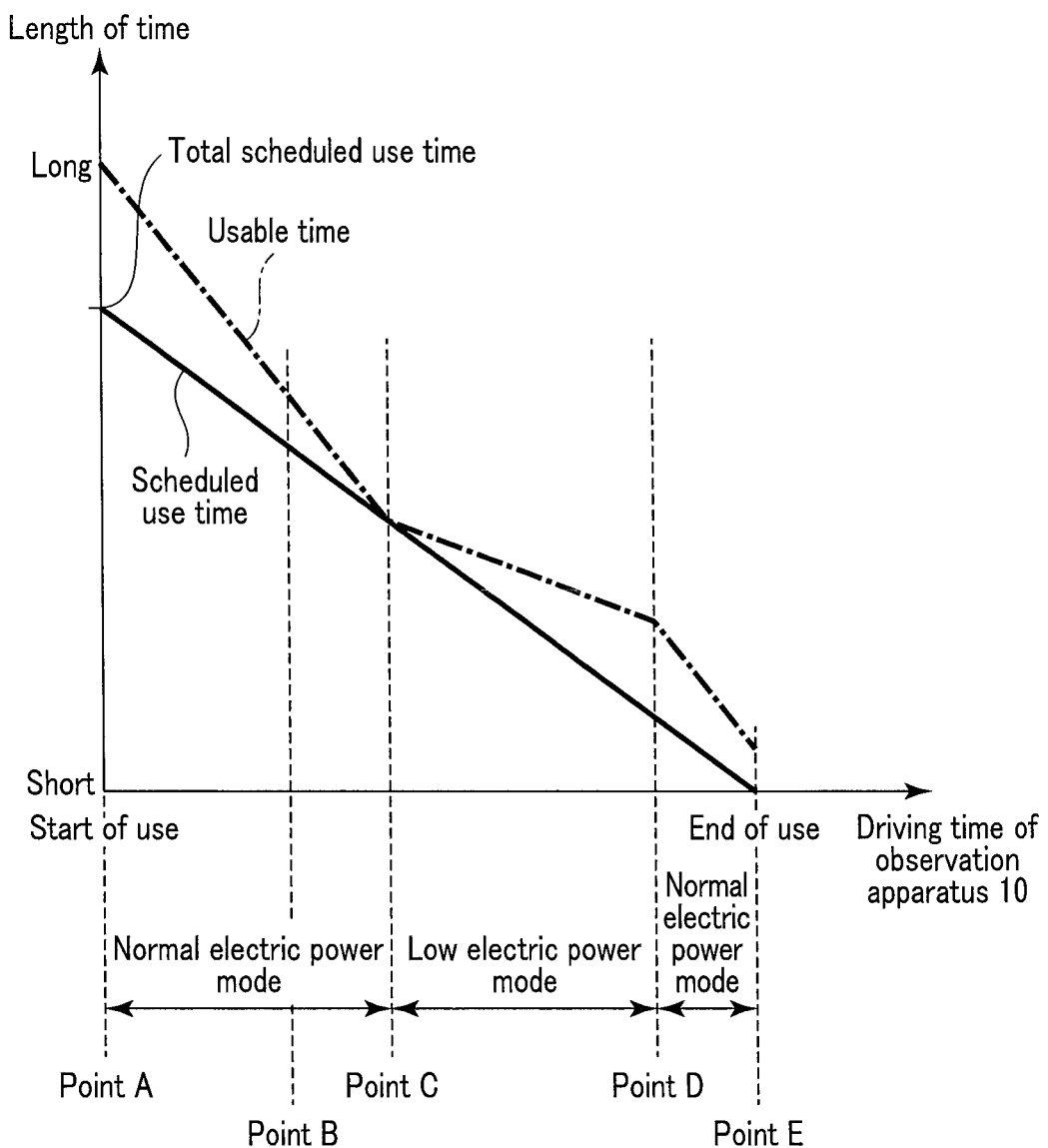
F I G. 3B

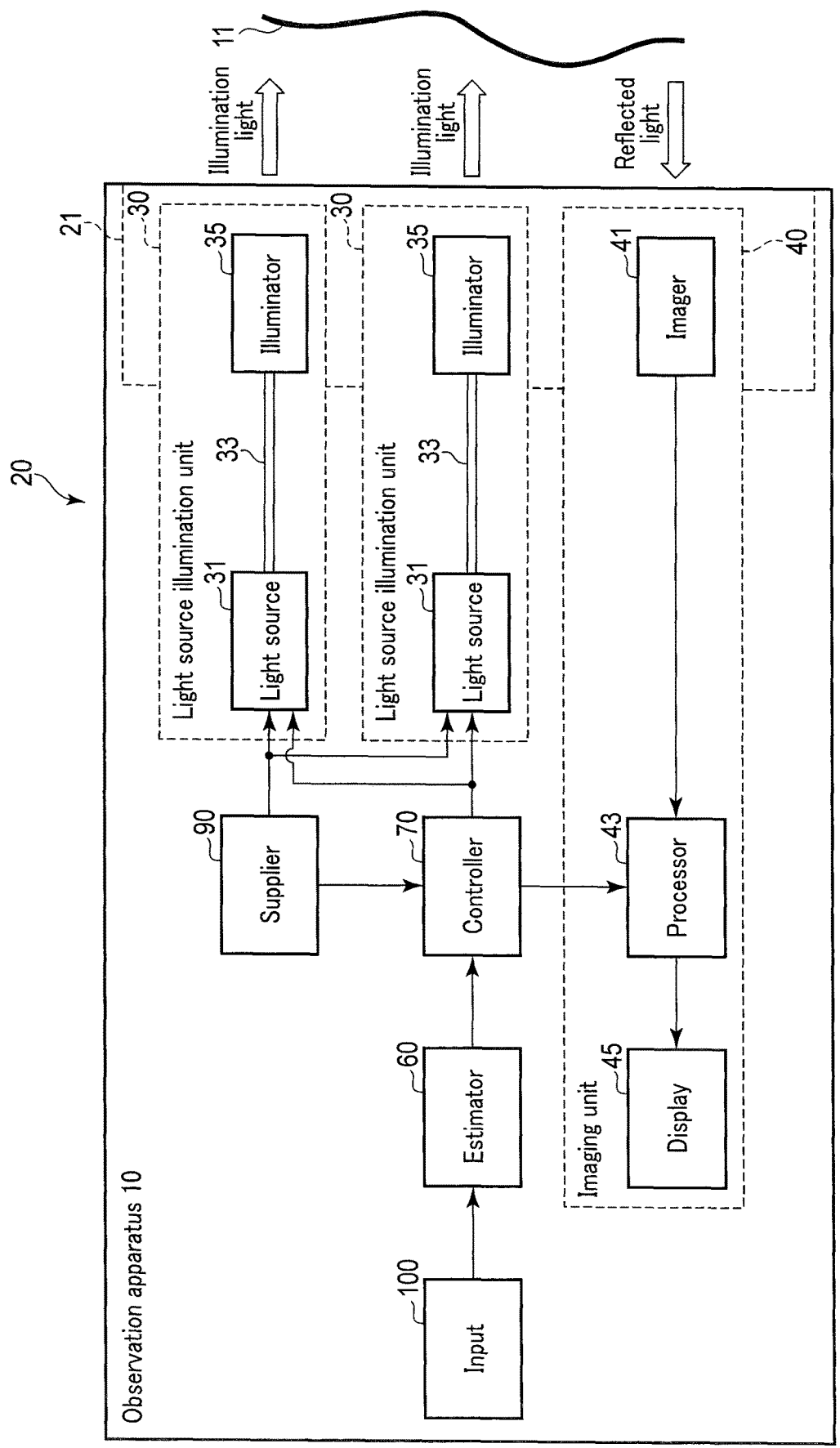
F I G. 4A

OBSERVATION APPARATUS AND ENDOSCOPE SYSTEM

CROSS-REFERENCE TO RELATED APPLICATIONS

This application is a Continuation Application of PCT Application No. PCT/JP2014/079453, filed Nov. 6, 2014, the entire contents of all of which are incorporated herein by reference.

BACKGROUND OF THE INVENTION

1. Field of the Invention

The present invention relates to an observation apparatus and an endoscope system having this observation apparatus.

2. Description of the Related Art

In general, an endoscope system has a light source which emits light. Electric power necessary for the operation of the light source accounts for most of electric power necessary for the operation of the whole endoscope system.

For example, Jpn. Pat. Appln. KOKAI Publication No. 2012-95911 discloses an endoscopic light source device which has a light source portion having a light source, and a battery to supply electric power to the light source portion and an endoscope main body. The endoscopic light source device saves electric power by pulse lighting of the light source.

BRIEF SUMMARY OF THE INVENTION

According to one aspect of an observation apparatus of the present invention, the observation apparatus comprises a light source illumination unit to illuminate illumination light to an observation target, and an imaging unit to image the observation target by receiving light reflected by the observation target to which the illumination light is illuminated, the observation apparatus comprises an estimator which estimates a current usage of the observation apparatus; and a controller which controls electric power consumption of the light source illumination unit on the basis of the current usage estimated by the estimator, wherein the light source illumination unit has operation modes including at least a normal electric power mode to operate with first electric power consumption, and a low electric power mode to operate with second electric power consumption lower than the first electric power consumption, and the controller selects at least one of the operation modes in accordance with the current usage, and controls the light source illumination unit in accordance with the selected operation mode.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute a part of the specification, illustrate embodiments of the invention, and together with the general description given above and the detailed description of the embodiments given below, serve to explain the principles of the invention.

FIG. 2A is a schematic diagram of the observation apparatus having a detector according to a first modification of the first embodiment;

FIG. 3A is a schematic diagram of the observation apparatus according to a second embodiment;

FIG. 3B is a graph showing the relation between usable time information, scheduled use time information, a normal electric power mode, and a low electric power mode in the driving time of the observation apparatus;

FIG. 4A is a schematic diagram of the observation apparatus according to a first modification of the second embodiment;

DETAILED DESCRIPTION OF THE INVENTION

Hereinafter, embodiments of the present invention will be described in detail with reference to the drawings. Some components are not shown in some of the drawings for the clarification of diagrammatic representation.

First Embodiment

[Configuration]

The first embodiment is described with reference to FIG. 1, FIG. 2A, FIG. 2B, and FIG. 2C.

[Observation Apparatus 10]

Figure 1:
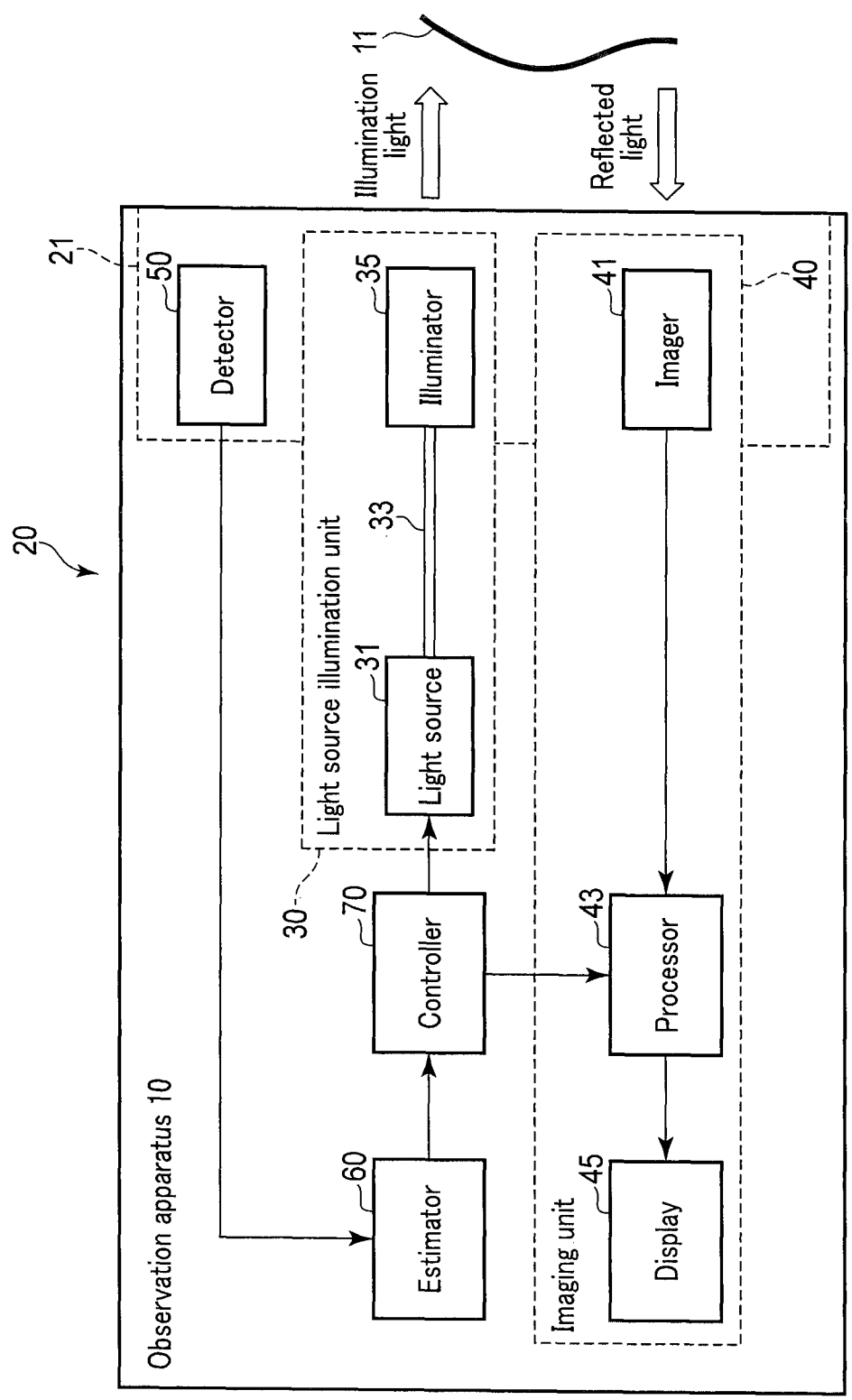
FIG. 1 is a schematic diagram of an observation apparatus according to a first embodiment of the present invention.

An observation apparatus 10 shown in FIG. 1 may be mounted on, for example, an endoscope system 20 having an endoscope. The endoscope is, for example, medically used, and uses the observation apparatus 10 to observe and image the inside of a lumen of a patient or the like. The endoscope according to the present embodiment is described as, for example, a medical endoscope, but does not need to be limited to this. It is also appropriate that the endoscope be an industrial endoscope or an insertion instrument such as a catheter. The observation apparatus 10 may also be mounted on an insertion system including the endoscope system 20.

As shown in FIG. 1, the observation apparatus 10 has a light source illumination unit 30 which illuminates illumination light to an observation target 11, and an imaging unit 40 which images the observation target 11 by receiving light reflected by the observation target 11 to which the illumination light is illuminated.

[Light Source Illumination Unit 30]

As shown in FIG. 1, the light source illumination unit 30 has a light source (light source portion) 31 which emits primary light, and a light guide (light guide member) 33 which guides the primary light emitted from the light source 31. The light source illumination unit 30 further has an illuminator (illumination portion) 35 which converts the optical characteristics of the primary light guided by the light guide 33 and illuminates secondary light different from the primary light to the observation target 11 as the illumination light.

Various kinds of light are used as the primary light in the light source 31 in accordance with the illuminator 35. The light source 31 has, for example, a laser light source which emits laser light.

The light guide 33 has one end portion optically connected to the light source 31, and the other end portion optically connected to the illuminator 35. The light guide 33 has, for example, linear optical fiber. The optical fiber may be a single optical fiber, or may be a bundle fiber.

The illuminator 35 faces the observation target 11 so that the illumination light can be illuminated to the observation target 11. Thus, the illuminator 35 is provided, for example, at a distal end portion of the observation apparatus 10 so that the illuminator 35 faces the observation target 11. When the observation apparatus 10 is mounted in the endoscope system 20, for example, the illuminator 35 is provided at a distal end of an insertion portion of the endoscope.

The illuminator 35 has, for example, a wavelength converting member which absorbs laser light that is primary light as excitation light, converts the wavelength of some of the absorbed laser light, and then emits the same to the outside. Such a wavelength converting member may have, for example, a fluorescent material which absorbs laser light that is the primary light and emits fluorescence as secondary light. The fluorescence which is wavelength-converted and the excitation light which is not wavelength-converted are emitted as illumination lights from the illuminator 35.

The illuminator 35 does not need to be limited to the above.

The illuminator 35 may have an element having a light diffusing function to increase the spread angle of the laser light which is the primary light and then emit the laser light as safe secondary light. In this case, for example, the illuminator 35 has a scattering member which scatters the primary light. The illuminator 35 may have, for example, an element having a function to phase-convert the laser light that is the primary light, reduce the coherency thereof, and prevent the production of speckles.

The illuminator 35 may be configured to emit illumination light having desired optical characteristics by an optical system such as a lens.

Such a light source illumination unit 30 has operation modes including at least a normal electric power mode to operate with first electric power consumption which is normal electric power consumption, and a low electric power mode to operate with second electric power consumption lower than the first electric power consumption.

For example, the low electric power mode refers to a mode in which the light source 31 is controlled by a later-described controller (control portion) 70 so that the brightness of the illumination light is lower and the amount of the illumination light is smaller than in the normal electric power mode due to electric power saving. For example, the normal electric power mode refers to a mode in which the light source 31 is controlled by the later-described controller 70 so that illumination light suitable to observation is generated.

[Imaging Unit 40]

As shown in FIG. 1, the imaging unit 40 has an imager (imaging element) 41 which images the observation target 11, a processor (processing portion) 43 which processes an imaging signal output from the imager 41 into a desired state, and a display (display portion) 45 which displays an image on the basis of the imaging signal processed by the processor 43.

The imager 41 faces the observation target 11 so that the imager 41 can image the observation target 11. Thus, the imager 41 is provided, for example, at the distal end portion of the observation apparatus 10 so that the imager 41 faces the observation target 11. When the observation apparatus 10 is mounted in the endoscope system 20, for example, the imager 41 is provided at the distal end of the insertion portion of the endoscope. The imager 41 is provided in the vicinity of the illuminator 35 so that the imager 41 is adjacent to the illuminator 35. If the illumination light is illuminated to the observation target 11, the illumination light is reflected by the observation target 11. The imager 41 receives this reflected light and thereby generates the imaging signal. The imager 41 has, for example, CCD or CMOS.

The processor 43 controls the imaging period (frame rate) of the imager 41. The processor 43 has, for example, a hardware circuitry including ASIC.

The display 45 has, for example, a monitor.

Such an imaging unit 40 may have operation modes including at least a normal electric power mode to operate with first electric power consumption which is normal electric power consumption, and a low electric power mode to operate with second electric power consumption lower than the first electric power consumption.

For example, the low electric power mode refers to a mode in which the processor 43 is controlled by the later-described controller 70 so that the brightness of the display 45 is lower, display information in the display 45 is less, and the number of times of imaging in the imager 41 is smaller than in the normal electric power mode due to electric power saving. For example, the normal electric power mode refers to a mode in which the processor 43 is controlled by the later-described controller 70 so that an image suitable to observation is generated.

[Detector 50]

As shown in FIG. 1, the observation apparatus 10 further has, for example, a detector (detection portion) 50 provided in a part 21 where the illuminator 35 of the light source illumination unit 30 that illuminates illumination light to the observation target 11 is provided. This part 21 is, for example, the distal end portion of the observation apparatus 10 facing the observation target 11 as described above. When the observation apparatus 10 is mounted in the endoscope system 20, for example, the detector 50 is provided at the distal end of the insertion portion of the endoscope. Thus, the detector 50 is provided, for example, at the distal end portion of the observation apparatus 10 and in the vicinity of the illuminator 35 so that the detector 50 is adjacent to the illuminator 35. The detector 50 may be provided, for example, at the distal end portion of the observation apparatus 10 and in the vicinity of the imager 41 so that the detector 50 is adjacent to the imager 41.

The detector 50 detects at least one piece of information including motion information which is information on the acceleration and velocity/angular velocity of the part 21, direction information for the part 21, and position information for the part 21 inside a subject having the observation target 11. The motion information, the direction information for the part 21, and a position change amount in the position information are operation amounts of the part 21.

Such a detector 50 has, for example, at least one of an acceleration sensor, an angular velocity sensor, a GPS, a sensor which specifies a position on the basis of radio intensity, and a geomagnetic sensor. The detector 50 outputs the detection result to an estimator 60 as a detection signal.

[Estimator 60]

As shown in FIG. 1, the observation apparatus 10 further has the estimator (estimation portion) 60 which estimates the current usage of the observation apparatus 10 including the part 21 on the basis of the detection result by the detector 50. The estimator 60 has, for example, a hardware circuitry including ASIC.

The estimator 60 estimates whether the current usage is a first usage in which the necessity of the operation of the light source illumination unit 30 is relatively great or a second usage in which the necessity of the operation of the light source illumination unit 30 is relatively small compared to the first usage. The estimator 60 may estimate whether the current usage is a first usage in which the necessity of the operation of the imaging unit 40 is relatively great or a second usage in which the necessity of the operation of the imaging unit 40 is relatively small compared to the first usage.

The estimator 60 estimates whether the current usage is the first usage or the second usage on the basis of at least one of the motion information for the part 21, the direction information for the part 21, and the position information for the part 21 inside the subject having the observation target 11 that are included in the detection result by the detector 50.

One example of how the estimator 60 estimates is described below.

The estimator 60 has predetermined reference values in advance, and compares the aforementioned information with the reference values. For example, the estimator 60 compares the motion information with the reference value for the motion information.

For example, when the motion information is substantially the same as the reference value, the situation is that the distal end portion is not moved, the current motion of the distal end portion is an average motion (posture) for use in observation, and an observation operation is in action. In other words, in a state where the distal end portion is not moved, the insertion portion has reached the observation target 11, and an observation operation is in action. Thus, the estimator 60 estimates that the observation operation of the observation apparatus 10 is in action. The estimator 60 estimates that the observation operation in action means a great necessity of illumination. Accordingly, the estimator 60 estimates that the current usage is the first usage.

The observation operation refers to, for example, the whole operation including an imaging operation of the imager 41, a display operation of the display 45 which works together with the imaging operation, and the operation of the light source illumination unit 30 which works together with the imaging operation.

For example, when the motion information is far away from the reference value, the situation is that the distal end portion is moved, the current motion of the distal end portion is greatly divergent from the average motion (posture) for use in observation, and the observation operation is out of action. In other words, during the movement of the distal end portion, the situation is that the insertion portion is being inserted or pulled out, or the distal end portion is outside the body and the apparatus is greatly moving due to conveyance or the like, and the observation operation is out of action. Thus, the estimator 60 estimates that the observation operation of the observation apparatus 10 is out of action. The estimator 60 estimates that the observation operation out of action means a small necessity of illumination. Accordingly, the estimator 60 estimates that the current usage is the second usage.

The estimator 60 compares the direction information with the reference value for the direction information in the following manner. For example, when the direction information is substantially the same as the reference value for the direction information, this shows that the current direction of the distal end portion is an average direction for use in observation. This is a situation in which the observation operation is in action. In other words, the direction of the distal end portion is the average direction for use in observation, the insertion portion has reached the observation target 11, and an observation operation is in action. Thus, the estimator 60 estimates that the observation operation of the observation apparatus 10 is in action. The estimator 60 estimates that the observation operation in action means a great necessity of illumination. Accordingly, the estimator 60 estimates that the current usage is the first usage.

For example, the situation in which the direction information is far away from the reference value for the direction information shows that the current direction of the distal end portion is divergent from the average direction for use in observation. That is, the direction of the distal end portion is not the average direction for use in observation, and the observation operation is out of action. In other words, in a state where the direction of the distal end portion is not the average direction for use in observation, the situation is that the insertion portion is being inserted or pulled out, or the distal end portion is outside the body and the apparatus is conveyed or held, and the observation operation is out of action. Thus, the estimator 60 estimates that the observation operation of the observation apparatus 10 is out of action. The estimator 60 estimates that the observation operation out of action means a small necessity of illumination. Accordingly, the estimator 60 estimates that the current usage is the second usage.

The estimator 60 compares the position information with the reference value for the position information in the following manner. For example, the situation in which the position information is substantially the same as the reference value for the position information is a situation in which the observation operation is in action. In other words, the insertion portion has reached the observation target 11, and the observation operation is in action. Thus, the estimator 60 estimates that the observation operation of the observation apparatus 10 is in action. The estimator 60 estimates that the observation operation in action means a great necessity of illumination. Accordingly, the estimator 60 estimates that the current usage is the first usage.

For example, the situation in which the position information is far away from the reference value for the position information shows that the observation operation is out of action. In other words, the situation is that the insertion portion is being inserted or pulled out, and the observation operation is out of action. Thus, the estimator 60 estimates that the observation operation of the observation apparatus 10 is out of action. The estimator 60 estimates that the observation operation out of action means a small necessity of illumination. Accordingly, the estimator 60 estimates that the current usage is the second usage.

The position information may have a change amount of a position. The position information should be treated in the same manner as the aforementioned motion information.

When the change amount of the position is greater than a reference value, the estimator 60 estimates that the insertion portion has reached the observation target 11 and that the observation operation of the observation apparatus 10 is in action. The estimator 60 estimates that the observation operation in action means a great necessity of illumination. Accordingly, the estimator 60 estimates that the current usage is the first usage.

When the change amount of the position is smaller than the reference value, the estimator 60 estimates that the observation apparatus 10 is placed on a desk or stored in a storage case or the like and that the observation operation of the observation apparatus 10 is out of action. The estimator 60 estimates that the observation operation out of action means a small necessity of illumination. Accordingly, the estimator 60 estimates that the current usage is the second usage.

The aforementioned operation amount (the motion information, the direction information, and the position change amount) is compared with the reference value for the operation amount in the following manner. For example, when the operation amount is far away from the reference value thereof, the estimator 60 estimates that the observation operation of the observation apparatus 10 is out of action. The estimator 60 estimates that the observation operation out of action means a small necessity of illumination. Accordingly, the estimator 60 estimates that the current usage is the second usage. Otherwise, when the operation amount is out of the reference range, the estimator 60 estimates that the observation operation of the observation apparatus 10 is out of action. The estimator 60 estimates that the observation operation out of action means a small necessity of illumination. Accordingly, the estimator 60 estimates that the current usage is the second usage.

The relation between the detector 50 and the estimator 60 does not need to be limited to the above. Modifications of this relation are described below.

[First Modification]

As shown in FIG. 2A, the detector 50 detects whether the observation apparatus 10 is grasped by an observer. Such a detector 50 is provided in, for example, a grasping portion 23 of the endoscope. The detector 50 has, for example, a pressure sensor or a capacitive sensor.

When the detector 50 detects that the observation apparatus 10 is grasped, the estimator 60 estimates that the current usage for observation is the first usage. In this case, the estimator 60 estimates that the observation apparatus 10 is grasped and that the observation operation of the observation apparatus 10 is in action.

When the detector 50 detects that the observation apparatus 10 is not touched, the estimator 60 estimates that the current usage for observation is the second usage. In this case, the estimator 60 estimates that the observation apparatus 10 is placed on a desk or stored in a storage case or the like and that the observation operation of the observation apparatus 10 is out of action.

[Second Modification]

Figure 2B:
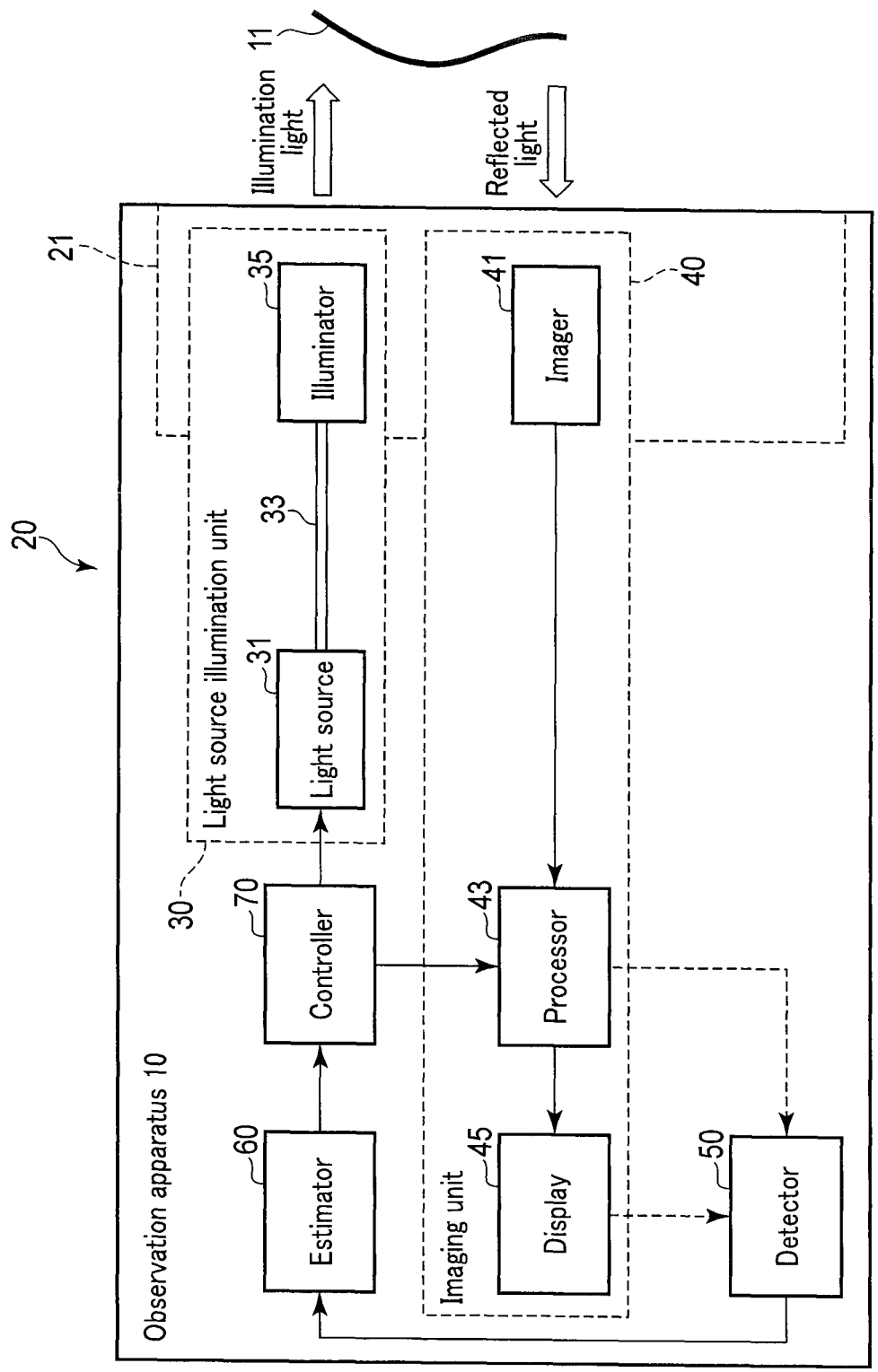
FIG. 2B is a schematic diagram of the observation apparatus having the detector according to a second modification of the first embodiment.

As shown in FIG. 2B, the detector 50 detects the state of an electric power supply of the processor 43 or the display 45.

For example, when the detector 50 detects that both the electric power supplies of the processor 43 and the display 45 are on, the estimator 60 estimates that the current usage for observation is the first usage. In this case, the estimator 60 estimates that the observation operation of the observation apparatus 10 is in action because the observation apparatus 10 is driven.

For example, when the detector 50 detects that the electric power supply of the processor 43 is off, the estimator 60 estimates that the current usage for observation is the second usage. In this case, the estimator 60 estimates that the observation operation of the observation apparatus 10 is out of action because the observation apparatus 10 is inactive.

In the above, the state of at least one of the electric power supplies of the processor 43 and the display 45 is detected, and the current usage of the whole observation apparatus 10 is thereby estimated. When one of the electric power supplies of the processor 43 and the display 45 is off, the estimator 60 estimates that the observation operation of the observation apparatus 10 is out of action because the observation apparatus 10 is inactive.

[Third Modification]

Figure 2C:
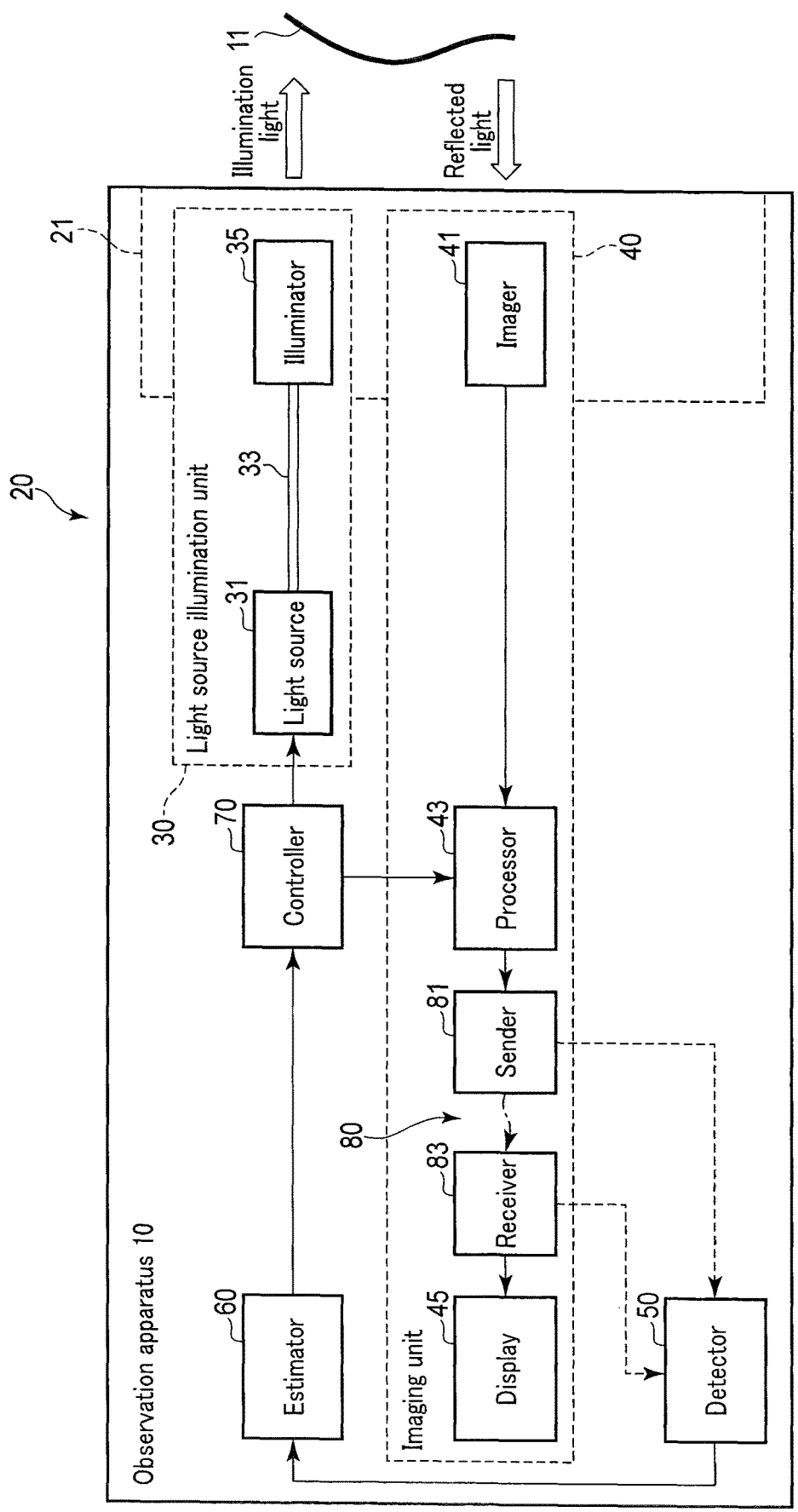
FIG. 2C is a schematic diagram of the observation apparatus having the detector according to a third modification of the first embodiment.

As shown in FIG. 2C, the detector 50 detects the connection state of a transmission path 80 to transmit the imaging signal output from the imager 41.

The transmission path 80 has, for example, a sender (send portion) 81 which is connected to the processor 43 and which sends the imaging signal output from the processor 43 by electric-wave radio, and a receiver (receive portion) 83 which is connected to the display 45 and which receives the imaging signal sent by the sender 81 and inputs the imaging signal to the display 45.

The detector 50 is connected to the sender 81 and the receiver 83, and detects the state of radio connection to the imaging signal in the sender 81 and the receiver 83 included in the transmission path 80.

The radio-type transmission path 80 may be provided between the imager 41 and the processor 43. In this case, the sender 81 is connected to the imager 41, and sends the imaging signal output from the imager 41. The receiver 83 is connected to the processor 43, and receives the imaging signal sent by the sender 81 and inputs the imaging signal to the processor 43.

The transmission path 80 does not need to be limited to the electric-wave radio, and may be available for infrared radio or radio other than the electric-wave radio. The transmission path 80 may have a wire including an electric wire. The electric wire may be detachable.

The detector 50 may be configured to be connected to one of the sender 81 and the receiver 83 as long as the detector 50 can detect the radio connection state in the sender 81 and the receiver 83.

When the detector 50 detects that the transmission path 80 is kept connected, the estimator 60 estimates that the current usage for observation is the first usage. In this case, the estimator 60 estimates that the observation operation of the observation apparatus 10 is in action or the observation operation is possible because the observation apparatus 10 is driven or the observation apparatus 10 can be driven.

When the detector 50 detects that the transmission path 80 is disconnected, the estimator 60 estimates that the current usage for observation is the second usage. In this case, the estimator 60 estimates that the observation operation of the observation apparatus 10 is out of action or the observation operation is impossible because the observation apparatus 10 is inactive or the observation apparatus 10 can not be driven.

[Fourth Modification]

Suppose that the observation apparatus 10 is placed, housed, or stored in a container such as a tray, a vat, or a holder.

The detector 50 is provided in the observation apparatus 10 and the container, and detects whether the observation apparatus 10 and the container are close to or in contact with each other. The detector 50 has, for example, an electromagnetic type sensor, a resistance type sensor, or a capacitance type sensor.

When the detector 50 detects that the observation apparatus 10 and the container are not close to or in contact with each other, the estimator 60 estimates that the observation apparatus 10 is not housed in the container, and estimates that the current usage for observation is the first usage. In this case, the estimator 60 estimates that the observation operation of the observation apparatus 10 is in action or the observation operation is possible because the observation apparatus 10 is driven or the observation apparatus 10 can be driven.

When the detector 50 detects that the observation apparatus 10 and the container are close to or in contact with each other, the estimator 60 estimates that the observation apparatus 10 is housed in the container, and estimates that the current usage for observation is the second usage. In this case, the estimator 60 estimates that the observation operation of the observation apparatus 10 is out of action because the observation apparatus 10 is inactive.

[Fifth Modification]

The detector 50 is provided in the part 21 where the imager 41 is provided, and detects the temperature of the part 21. The temperature of the part 21 indicates, for example, the temperature inside the part 21.

When the estimator 60 judges that the detected temperature is higher than a preset reference value, the estimator 60 estimates that the part 21 is inserted in a lumen of a body cavity, and estimates that the current usage for observation is the first usage. The preset reference value refers to, for example, a temperature substantially equal to a body temperature.

When the estimator 60 judges that the detected temperature is lower than the preset reference value, the estimator 60 estimates that the part 21 is disposed outside the lumen of the body cavity, and estimates that the current usage for observation is the second usage.

[Sixth Modification]

The detector 50 is provided in the display 45, and detects whether the eyes or face of the observer is directed to the display 45. The detector 50 has a visual line sensor or a face recognition device.

When the detector 50 detects that the eyes or face is directed to the display 45, the estimator 60 estimates that the current usage for observation is the first usage.

When the detector 50 detects that the eyes or face is not directed to the display 45, the estimator 60 estimates that the current usage for observation is the second usage.

[Others]

In each detection operation described above, more than one detection operation may be performed, and the estimator 60 may finally estimate the current usage for observation on the basis of more than one detection result.

In each estimation operation described above, after more than one estimation operation are performed, the estimator 60 may finally estimate whether the current usage for observation is the first usage or the second usage on the basis of more than one estimation result.

In each estimation operation described above, if the estimation result is maintained for a certain period of time, the estimator 60 may finally estimate whether the current usage for observation is the first usage or the second usage.

The detector 50 may always keep detecting, or may start detection by the operation of an unshown switch. Thus, desired detection timing, a desired detection period, and the like are set. When the observation apparatus 10 is driven by a battery, the detector 50 may start detection by the timing of the replacement of the battery. The detector 50 always outputs the detection result, or outputs the detection result by desired timing.

[Controller 70]

As shown in FIG. 1, the observation apparatus 10 further has the controller 70. The controller 70 has, for example, a hardware circuitry including ASIC.

The controller 70 controls the electric power consumption of the light source 31 of the light source illumination unit 30 on the basis of the current usage estimated by the estimator 60.

The controller 70 selects, for example, one of the operation modes of the light source illumination unit 30 in accordance with the current usage, and controls the light source illumination unit 30 in accordance with the selected operation mode. The controller 70 selects, for the light source illumination unit 30, the normal electric power mode from among the operation modes in the first usage, and selects the low electric power mode from among the operation modes in the second usage.

The controller 70 may control the electric power consumption of the processor 43 of the imaging unit 40 on the basis of the current usage estimated by the estimator 60. The controller 70 selects, for example, one of the operation modes of the imaging unit 40 in accordance with the current usage, and controls the light source illumination unit 30 in accordance with the selected operation mode. The controller 70 selects, for the imaging unit 40, the normal electric power mode from among the operation modes in the first usage, and selects the low electric power mode from among the operation modes in the second usage.

Specific control of the controller 70 will be described later.

[Observation Operation]

The light source 31 emits primary light. The primary light is guided by the light guide 33, and converted into secondary light by the illuminator 35. Illumination light which is the secondary light is illuminated to the observation target 11. The illumination light is reflected by the observation target 11, and received by the imager 41. The imager 41 generates an imaging signal by receiving the illumination light. The processor 43 processes the imaging signal, and the display 45 displays an image on the basis of the imaging signal processed by the processor 43.

[Detection Operation]

If the distal end portion of the observation apparatus 10 moves, the detector 50 detects, for example, the motion information for the part 21, and outputs the detection result to the estimator 60 as a detection signal.

[Estimation Operation]

The estimator 60 estimates whether the current usage is the first usage or the second usage on the basis of the detection result by the detector 50.

[Control Operation]

[When Current Usage is the First Usage, Normal Electric Power Mode]

When the estimator 60 estimates that the current usage is the first usage, the controller 70 controls the light source 31 on the basis of the estimation result by the estimator 60 so that the light source 31 is driven in the normal electric power mode. The controller 70 may control the processor 43 on the basis of this estimation result so that the imaging unit 40 is driven in the normal electric power mode. The timing by which the controller 70 controls the light source 31 is substantially the same as the timing by which the controller 70 controls the processor 43.

[When Current Usage is the Second Usage, Low Electric Power Mode]

When the estimator 60 estimates that the current usage is the second usage, the controller 70 controls the light source 31 on the basis of this estimation result by the estimator 60 so that the light source 31 is driven in the low electric power mode. The controller 70 may control the processor 43 on the basis of this estimation result so that the imaging unit 40 is driven in the low electric power mode. The timing by which the controller 70 controls the light source 31 is substantially the same as the timing by which the controller 70 controls the processor 43.

When the operation mode of the light source illumination unit 30 and the operation mode of the imaging unit 40 are the low electric power modes, the controller 70 controls the light source 31 of the light source illumination unit 30 and the processor 43 of the imaging unit 40 so that the luminance of the imaging signal output from the imager 41 of the imaging unit 40 in the low electric power mode is kept at the luminance of the imaging signal output from the imager 41 of the imaging unit 40 in the normal electric power mode, even if the electric power consumption of the light source illumination unit 30 is the second electric power consumption. The luminance of the imaging signal refers to the brightness of the image displayed by the display 45.

In this case, the controller 70 controls the processor 43 so that the frame rate of the imager 41 in the low electric power mode may be lower than the frame rate of the imager 41 in the normal electric power mode. The processor 43 controls the imager 41 and circuitry (circuitry portion) provided around the imager 41 so that the frame rate may be lower as described above. For example, the frame rate in the normal electric power mode is 60 frames per second, and the frame rate in the low electric power mode is 30 frames per second, 20 frames per second, or 15 frames per second. It is also appropriate that the frame rate in the low electric power mode be an integer fraction of the frame rate in the normal electric power mode.

When the operation mode of the light source illumination unit 30 and the operation mode of the imaging unit 40 are the low electric power modes, the controller 70 controls the light source 31 of the light source illumination unit 30 and the processor 43 of the imaging unit 40 so that the frame rate of the imager 41 in the low electric power mode may be lower than the frame rate of the imager 41 in the normal electric power mode and the light source illumination unit 30 may illuminate illumination light in a period of the exposure of the imager 41. The light source 31 turns on so that the integration value of the illumination light amount in the exposure period of one imaging frame of the imager 41 may be equal. When the frame rate decreases without any change in the exposure period of the imager 41, the light source 31 should turn on in the exposure period alone without any change in the light amount whether the mode is the low electric power mode or the normal electric power mode. When the frame rate decreases so that the exposure period of the imager 41 may be longer, the light source 31 may reduce the light amount to maintain the integration value of the illumination light amount. In each case, the illumination light amount per unit time in the low electric power mode is lower than the illumination light amount per unit time in the normal electric power mode. Thus, the electric power consumption in the low electric power mode is lower than the electric power consumption in the normal electric power mode. Although the illumination light amount is lower in the above, the light source illumination unit 30 emits the illumination light in the period of the exposure of the imager 41.

Therefore, the luminance of the image displayed by the display 45 in the low electric power mode is kept at the luminance of the image displayed by the display 45 in the normal electric power mode, so that the brightness of the image in the low electric power mode will be substantially the same as the brightness of the image in the normal electric power mode. This prevents the image in the low electric power mode from being darker than the image in the normal electric power mode.

Instead of the reduction of the frame rate, non-lighting frames in which the emission operation of the illumination light stops may be inserted to thin out lighting frames in which the emission operation of the illumination light is performed. The display 45 skips the non-lighting frames, and only displays the lighting frames. As a result, the illumination light amount per unit time in the low electric power mode is lower than the illumination light amount per unit time in the normal electric power mode. Thus, the electric power consumption in the low electric power mode is lower than the electric power consumption in the normal electric power mode.

When the operation mode of the light source illumination unit 30 and the operation mode of the imaging unit 40 are the low electric power modes, the controller 70 may control the light source illumination unit 30 and the imaging unit 40 so that an imaging gain for the imaging signal of the imager 41 in the low electric power mode may be greater than an imaging gain for the imaging signal of the imager 41 in the normal electric power mode and the illumination light amount of the light source illumination unit 30 in the low electric power mode is smaller than the illumination light amount of the light source illumination unit 30 in the normal electric power mode. The imaging gain is amplified by an unshown amplifier (amplifier portion) provided in the imager 41 or the processor 43. The amount of light which is illuminated to the observation target 11 and then enters the imager 41 decreases, but the imaging gain for the imaging signal output from the imager 41 is increased by the amplifier. Thus, the level of the imaging signal input to the processor 43 in the low electric power mode is kept at the level of the imaging signal input to the processor 43 in the normal electric power mode. Therefore, the illumination light amount per unit time in the low electric power mode is lower than the illumination light amount per unit time in the normal electric power mode, but the luminance of the image displayed by the display 45 in the low electric power mode is kept at the luminance of the image displayed by the display 45 in the normal electric power mode. The brightness of the image in the low electric power mode is substantially the same as the brightness of the image in the normal electric power mode. This prevents the image in the low electric power mode from being darker than the image in the normal electric power mode.

As described above, the electric power consumption of the light source illumination unit 30 which is high in electric power consumption among the members and units of the observation apparatus 10 decreases in response to the current usage of the observation apparatus 10 in the low electric power mode. Thus, electric power is saved in accordance with the current usage of the observation apparatus 10. The time in which the observation apparatus 10 is usable then increases.

Advantageous Effects

In the present embodiment, the estimator 60 estimates the current usage so that electric power can be saved in accordance with the current usage. In the present embodiment, the time in which the observation apparatus 10 is usable can be then increased.

In the present embodiment, the estimator 60 can more accurately estimate the current usage of the observation apparatus 10 in accordance with the detection result by the detector 50 provided in the part 21 where the illuminator 35 is provided.

The estimator 60 estimates the current usage on the basis of various types of detection results, more than one detection result, more than one estimation result, and the estimation result maintained for a certain period of time. Thus, it is possible to more accurately estimate the current usage of the observation apparatus 10.

In the present embodiment, even if the low electric power mode is performed, the brightness of the image in the low electric power mode can be substantially the same as the brightness of the image in the normal electric power mode.

The display 45 may be omitted. The observation apparatus 10 may have a storage (storage unit) to store image information which is the imaging signal processed by the processor 43.

When the low electric power mode is selected, the display 45 may display the fact of this selection. The observation apparatus 10 may also have a report unit which reports to the observer that the low electric power mode is selected. The report unit reports, for example, by sound.

First Modification of First Embodiment

Although the normal electric power mode and the low electric power mode are used to describe the operation modes of the light source illumination unit 30 in the present embodiment, the operation modes do not need to be limited to the above.

The operation modes of the light source illumination unit 30 may further include an intermediate electric power mode to operate with third electric power consumption lower than the first electric power consumption and higher than the second electric power consumption.

In this case, the estimator 60 further estimates, on the basis of the detection result by the detector 50, a third usage in which the necessity of the operation of the light source illumination unit 30 is relatively small compared to the first usage and relatively great compared to the second usage, and a transition state which is a state of transition from the first usage to the second usage or from the second usage to the first usage. The third usage indicates, for example, a state in which the first usage and the second usage can not be clearly distinguished from each other during the detection operation by the detector 50 or during radio connection.

The controller 70 selects, for the light source illumination unit 30, the intermediate electric power mode from among the operation modes in the third usage and the transition state. The controller 70 may select the intermediate electric power mode for the imaging unit 40 in the third usage and the transition state.

Although the controller selects one of the operation modes in the above, the controller does not need to be limited to this. For example, the controller may select at least one of the operation modes or select a combination of the operation modes in accordance with the current usage.

Second Embodiment

[Configuration]
The differences between the first embodiment and the second embodiment are only described below with reference to FIG. 3A and FIG. 3B.
[Observation Apparatus 10]
As shown in FIG. 3A, the detector 50 is omitted.
[Supplier 90]
As shown in FIG. 3A, the observation apparatus 10 further has a supplier (supply portion) 90 which supplies, for example, electric power to the observation apparatus 10, in addition to the light source illumination unit 30, the imaging unit 40, the estimator 60, and the controller 70. Because the supplier 90 supplies most of the electric power to the light source 31 of the light source illumination unit 30 and the controller 70, this fact is only indicated by arrows in FIG. 3A.

The supplier 90 has a battery. The battery has a primary battery or a secondary battery, such as a lithium ion charging battery or a nickel metal-hydride charging battery. Such a battery supplies limited electric power. The supplier 90 may have not only a battery which creates electric power by common chemical changes but also members that can supply limited electric power, such as an electric double layer capacitor, an electric power storage device using kinetic energy such as a fly wheel, and an electric generator which is operated by fuel. The supplier 90 directly supplies electric power to each part. The observation apparatus 10 may have a radio electric supply system which is provided between the supplier 90 and the light source 31 and which supplies electricity by radio or the like. Alternatively, the supplier 90 may be provided outside the observation apparatus 10, and the radio electric supply system may be provided between the supplier 90 and the observation apparatus 10.
[Input 100]
As shown in FIG. 3A, the observation apparatus 10 further has an input (input portion) 100 to input total scheduled use time information having a total scheduled use time of the observation apparatus 10 scheduled from the start of the use of the observation apparatus 10 to the end of the use of the observation apparatus 10. This information may be input before the start of the operation of the observation apparatus 10 or may be input as needed while the observation apparatus 10 is in operation. The information is input by the observer. The input 100 has, for example, a keyboard.

The total scheduled use time information may have a time calculated on the basis of at least one of, for example, an observation part of the observation target 11 scheduled to be observed, the kind of observation, and the procedure of the observation. In this case, for example, the total scheduled use time information has, for example, the time necessary for the observation of the observation part of the observation target 11. Time information corresponding to the observation part, time information corresponding to the kind, and time information corresponding to the procedure may be stored in an unshown storage (storage unit) as a data table in advance. The observation part of the observation target 11, the kind of observation, and the procedure of the observation above are input by the input 100.
[Estimator 60]
The estimator 60 estimates scheduled use time information having a future scheduled use time of the observation apparatus 10 including the part 21 on the basis of the input result by the input 100.

Specifically, the estimator 60 estimates the scheduled use time information having the scheduled use time of the observation apparatus 10 on the basis of the total scheduled use time information having the aforementioned total scheduled use time of the observation apparatus 10 scheduled from the start of the use of the observation apparatus 10 to the end of the use of the observation apparatus 10. The scheduled use time is a time scheduled from the point of the estimation of the scheduled use time to the end of the use of the observation apparatus 10. As described above, the total scheduled use time information is input to the estimator 60 from the input 100. The estimator 60 has a timer which starts the measurement of time simultaneously with the start of the operation of the observation apparatus 10. The estimator 60 subtracts the operating time of the observation apparatus 10 measured by the timer from the total scheduled use time information input from the input 100, and calculates the scheduled use time information having the aforementioned use time which is a remaining time. The estimator 60 outputs the scheduled use time information to the controller 70.

The estimator 60 may estimate the scheduled use time information in accordance with time information calculated on the basis of at least one of the observation part of the observation target 11 scheduled to be observed, the kind of observation, and the procedure of the observation. The observation part and others are input to the estimator 60 from the input 100.

[Controller 70]

The controller 70 obtains remaining capacity information from the supplier 90. The remaining capacity information indicates the capacity of electric power that can be supplied by the supplier 90 in the future, i.e., the remaining capacity of the supplier 90. The controller 70 may obtain the remaining capacity information on the basis of an inter-terminal voltage of the supplier 90, or may obtain the remaining capacity information by accumulating electric power consumed. The controller 70 may obtain the remaining capacity information by using a procedure of prediction through the impedance of the supplier 90, the ambient temperature, and a combination of such information.

The controller 70 previously stores electric power consumption information having the electric power consumption of the light source 31. The controller 70 calculates usable time information having the time in which the observation apparatus 10 is usable on the basis of the remaining capacity information and the electric power consumption information. The usable time information indicates, for example, how long the light source 31 can be driven with the remaining capacity.

The controller 70 controls the electric power consumption of the light source illumination unit 30 on the basis of the scheduled use time information estimated by the estimator 60. The controller 70 selects, for example, one of the operation modes of the light source illumination unit 30 in accordance with a use schedule, and controls the light source illumination unit 30 in accordance with the selected operation mode.

As shown in FIG. 3B, at the start of the use of the observation apparatus 10, the usable time calculated on the basis of the remaining capacity information and the electric power consumption information is longer than the scheduled use time calculated on the basis of the total scheduled use time, as indicated by a point A in FIG. 3B. The usable time and the scheduled use time decrease simultaneously with the start of the operation of the observation apparatus 10. The scheduled use time always decreases at a constant rate. In contrast, the decrease rate of the usable time varies according to the operation modes. The decrease rate of the usable time is different from the decrease rate of the scheduled use time. As shown in FIG. 3B, the decrease rate of the usable time in the normal electric power mode is higher than the decrease rate of the scheduled use time. The decrease rate of the usable time in the low electric power mode is lower than the decrease rate of the usable time and the decrease rate of the scheduled use time in the normal electric power mode.

Thus, as shown in FIG. 3B, in the normal electric power mode, the usable time gradually approaches the scheduled use time after the start of the use of the observation apparatus 10 (e.g. see a point B).

If the usable time reaches the scheduled use time (e.g. see a point C), the low electric power mode is selected, and the usable time departs from the scheduled use time.

In the above, the controller 70 compares the scheduled use time information estimated by the estimator 60 with the usable time information calculated by the controller 70. As indicated by the point B in FIG. 3B, when the controller 70 judges that the usable time in the usable time information is longer than the scheduled use time in the scheduled use time information, the controller 70 keeps the light source 31 of the light source illumination unit 30 in the normal electric power mode.

When the controller 70 judges that the usable time in the usable time information is the same as the scheduled use time in the scheduled use time information as indicated by the point C in FIG. 3B or judges that the scheduled use time in the scheduled use time information is longer than the usable time in the usable time information, which is, however, not shown, the controller 70 selects the low electric power mode for the light source 31 of the light source illumination unit 30.

When the usable time−the scheduled use time>0 (e.g. see a point D), the controller 70 may select the normal electric power mode. In this case, it is not necessary to limit to "0", and a threshold may be set, and a value in which the scheduled use time is subtracted from the usable time may be compared with the threshold. When the subtracted value is higher than the threshold as indicated by the point D in FIG. 3B, the controller 70 selects the normal electric power mode.

If the scheduled use time reaches 0 (e.g. see a point E), the use of the observation apparatus 10 ends.

[Operation Method]

The supplier 90 is mounted in the observation apparatus 10 so that the supplier 90 can supply electric power to, for example, the light source 31.

The input 100 inputs the total scheduled use time information having the total scheduled use time.

If the use of the observation apparatus 10 is started as indicated by the point A in FIG. 3B, the operation of the observation apparatus 10 is also started. At the same time, the total scheduled use time in the total scheduled use time information is input to the estimator 60 from the input 100. At the point A, the scheduled use time is equal to the total scheduled use time.

During the operation of the observation apparatus 10, the following operations are periodically performed in the estimator 60 and the controller 70. Each piece of information below is information at the point where the operation is performed, and is always updated.

If the total scheduled use time in the total scheduled use time information is input to the estimator 60 from the input 100, the estimator 60 initializes (resets) the time (count) in the timer. At the same time, the estimator 60 subtracts the operating time of the observation apparatus 10 measured by the timer from the total scheduled use time, and calculates the scheduled use time.

The controller 70 calculates the usable time information having the usable time on the basis of the remaining capacity information obtained from the supplier 90 and the previously stored electric power consumption information.

The controller 70 compares the scheduled use time in the scheduled use time information estimated by the estimator 60 with the usable time in the usable time information calculated by the controller 70.

In the case shown in the example of FIG. 3B, the electric power consumption information for the light source 31 for use in the calculation of the usable time information shows the electric power consumption less than the actual electric power consumption of the light source 31. Thus, as shown in FIG. 3B, the usable time decreases earlier (with a steeper inclination) than the scheduled use time. As indicated by the point B in FIG. 3B, the controller 70 keeps the light source 31 of the light source illumination unit 30 and the processor 43 of the imaging unit 40 in the normal electric power mode as long as the controller 70 judges that the usable time is longer than the scheduled use time. If the controller 70 judges that the scheduled use time is the same as the usable time as indicated by the point C in FIG. 3B or the controller 70 judges that the scheduled use time is longer than the usable time, which is, however, not shown, the controller 70 selects the low electric power modes for the light source 31 of the light source illumination unit 30 and the processor 43 of the imaging unit 40.

[Control Operation]

[Normal Electric Power Mode]

As described above, when the controller 70 judges that the usable time is longer than the scheduled use time as indicated by the point B in FIG. 3B, the controller 70 keeps the light source 31 of the light source illumination unit 30 and the processor 43 of the imaging unit 40 in the normal electric power mode. The timing by which the controller 70 controls the light source 31 is substantially the same as the timing by which the controller 70 controls the processor 43.

[Low Electric Power Mode]

As described above, when the controller 70 judges that the scheduled use time is the same as the usable time as indicated by the point C in FIG. 3B or judges that the scheduled use time is longer than the usable time, which is, however, not shown, the controller 70 selects the low electric power modes for the light source illumination unit 30 and the processor 43 of the imaging unit 40. The timing by which the controller 70 controls the light source 31 is substantially the same as the timing by which the controller 70 controls the processor 43.

In the case where the operation mode of the light source illumination unit 30 and the operation mode of the imaging unit 40 are the low electric power modes, the controller 70 controls the light source 31 of the light source illumination unit 30 and the processor 43 of the imaging unit 40 so that the luminance of the imaging signal output from the imager 41 of the imaging unit 40 in the low electric power mode is kept at the luminance of the imaging signal output from the imager 41 of the imaging unit 40 in the normal electric power mode, even when the electric power consumption of the light source illumination unit 30 is the second electric power consumption. The luminance of the imaging signal refers to the brightness of the image displayed by the display 45.

In this case, the controller 70 controls the processor 43 so that the frame rate of the imager 41 in the low electric power mode may be lower than the frame rate of the imager 41 in the normal electric power mode. The processor 43 controls the imager 41 and the circuitry provided around the imager 41 so that the frame rate may be lower as described above. For example, the frame rate in the normal electric power mode is 60 frames per second, and the frame rate in the low electric power mode is 30 frames per second, 20 frames per second, or 15 frames per second. It is also appropriate that the frame rate in the low electric power mode be an integer fraction of the frame rate in the normal electric power mode.

When the operation mode of the light source illumination unit 30 and the operation mode of the imaging unit 40 are the low electric power modes, the controller 70 controls the light source 31 of the light source illumination unit 30 and the processor 43 of the imaging unit 40 so that the frame rate of the imager 41 in the low electric power mode is lower than the frame rate of the imager 41 in the normal electric power mode and the light source illumination unit 30 illuminates illumination light in a period of the exposure of the imager 41. The light source 31 turns on so that the integration value of the illumination light amount in the exposure period of one imaging frame of the imager 41 may be equal. When the frame rate decreases without any change in the exposure period of the imager 41, the light source 31 should turn on in the exposure period alone without any change in the light amount whether the mode is the low electric power mode or the normal electric power mode. When the frame rate decreases so that the exposure period of the imager 41 may be longer, the light source 31 may reduce the light amount to maintain the integration value of the illumination light amount. In each case, the illumination light amount per unit time in the low electric power mode is lower than the illumination light amount per unit time in the normal electric power mode. Thus, the electric power consumption in the low electric power mode is lower than the electric power consumption in the normal electric power mode. Although the illumination light amount is lower in the above, the light source illumination unit 30 illuminates the illumination light in the period of the exposure of the imager 41. Therefore, the luminance of the image displayed by the display 45 in the low electric power mode is kept at the luminance of the image displayed by the display 45 in the normal electric power mode, so that the brightness of the image in the low electric power mode will be substantially the same as the brightness of the image in the normal electric power mode. This prevents the image in the low electric power mode from being darker than the image in the normal electric power mode.

Instead of the reduction of the frame rate, non-lighting frames in which the emission operation of the illumination light stops may be inserted to thin out lighting frames in which the emission operation of the illumination light is performed. The display 45 skips the non-lighting frames, and only displays the lighting frames. As a result, the illumination light amount per unit time in the low electric power mode is lower than the illumination light amount per unit time in the normal electric power mode. Thus, the electric power consumption in the low electric power mode is lower than the electric power consumption in the normal electric power mode.

When the operation mode of the light source illumination unit 30 and the operation mode of the imaging unit 40 are the low electric power modes, the controller 70 may control the light source illumination unit 30 and the imaging unit 40 so that an imaging gain for the imaging signal of the imager 41 in the low electric power mode is greater than an imaging gain for the imaging signal of the imager 41 in the normal electric power mode and the illumination light amount of the light source illumination unit 30 in the low electric power mode is smaller than the illumination light amount of the light source illumination unit 30 in the normal electric power mode. The imaging gain is amplified by an unshown amplifier (amplifier portion) provided in the imager 41 or the processor 43. The amount of light which is illuminated to the observation target 11 and then enters the imager 41 decreases, but the imaging gain for the imaging signal output from the imager 41 is increased by the amplifier. Thus, the level of the imaging signal input to the processor 43 in the low electric power mode is kept at the level of the imaging signal input to the processor 43 in the normal electric power mode. Therefore, the illumination light amount per unit time in the low electric power mode is lower than the illumination light amount per unit time in the normal electric power mode, but the luminance of the image displayed by the display 45 in the low electric power mode is kept at the luminance of the image displayed by the display 45 in the normal electric power mode. The brightness of the image in the low electric power mode is substantially the same as the brightness of the image in the normal electric power mode. This prevents the image in the low electric power mode from being darker than the image in the normal electric power mode.

As described above, the electric power consumption of the light source illumination unit 30 which is high in electric power consumption among the members and units of the observation apparatus 10 decreases in response to the future scheduled use time of the observation apparatus 10 in the low electric power mode. Thus, electric power is saved in accordance with the future scheduled use time of the observation apparatus 10. The time in which the observation apparatus 10 is usable then increases.

Advantageous Effects

In the present embodiment, the observation apparatus 10 is operated by the limited electric power supplied from the supplier 90. When the scheduled use time which is updated in advance or as needed is the same as or longer than the usable time, the light source 31 is driven in the low electric power mode, as indicated by the part between the point C and the point D in FIG. 3B. When the usable time is longer than the scheduled use time as indicated by the part between the point A and the point C in FIG. 3B, the light source 31 is driven in the normal electric power mode. Consequently, in the present embodiment, electric power can be saved in accordance with the future scheduled use time. In the present embodiment, the time in which the observation apparatus 10 is usable can be then increased.

The above contents have been described by use of the light source 31 as an example, but may be applied to the imaging unit 40.

Although not shown, the observation apparatus 10 may have an electric power detection unit which detects electric power consumption. The electric power detection unit detects electric power consumption in a certain period immediately before the controller 70 calculates the usable time information. The detected electric power consumption is used to calculate the usable time information.

The observation apparatus 10 may have a prediction system which predicts electric power consumption from the actual operating states of the light source 31 and the observation apparatus 10, and a prediction system which predicts future electric power consumption from electric power consumption during past operations. Thus, the usable time information is accurately calculated.

The battery which is the supplier 90 is configured to be attachable to and detachable from the observation apparatus 10, and the counting of the timer may be reset when the supplier 90 is connected to the observation apparatus 10.

The total scheduled use time information may be input as information previously stored in the unshown storage instead of being input every time. This saves the time for inputting.

The total scheduled use time information may be input when the observation apparatus 10 is in use. In this case, the counting of the timer is reset at the time of the input.

The controller 70 may calculate an electric power amount necessary for the operation for the scheduled use time on the basis of the electric power consumption information, and compare the necessary electric power amount with the remaining capacity information. When the remaining capacity information is lower than the necessary electric power amount, the controller 70 selects the low electric power modes.

When the usable time–the scheduled use time>0, the controller 70 may select the normal electric power mode. In this case, it is not necessary to limit to "0", and a threshold may be set, and a value in which the scheduled use time is subtracted from the usable time may be compared with the threshold. When the subtracted value is higher than the threshold as indicated by the point D in FIG. 3B, the controller 70 selects the normal electric power mode. This can inhibit a phenomenon in which the modes are unnecessarily frequently selected.

The controller 70 may calculate the second electric power consumption in the low electric power mode, control the light source 31 with the second electric power consumption, and update the usable time information on the basis of the information on the second electric power consumption so that the usable time information calculated from the remaining capacity information may surpass the scheduled use time information.

The past operating state of the light source 31 may be stored in the unshown storage. The electric power consumption of the light source 31 in operation may be calculated on the basis of the operating state stored in this storage.

Figure 3C:
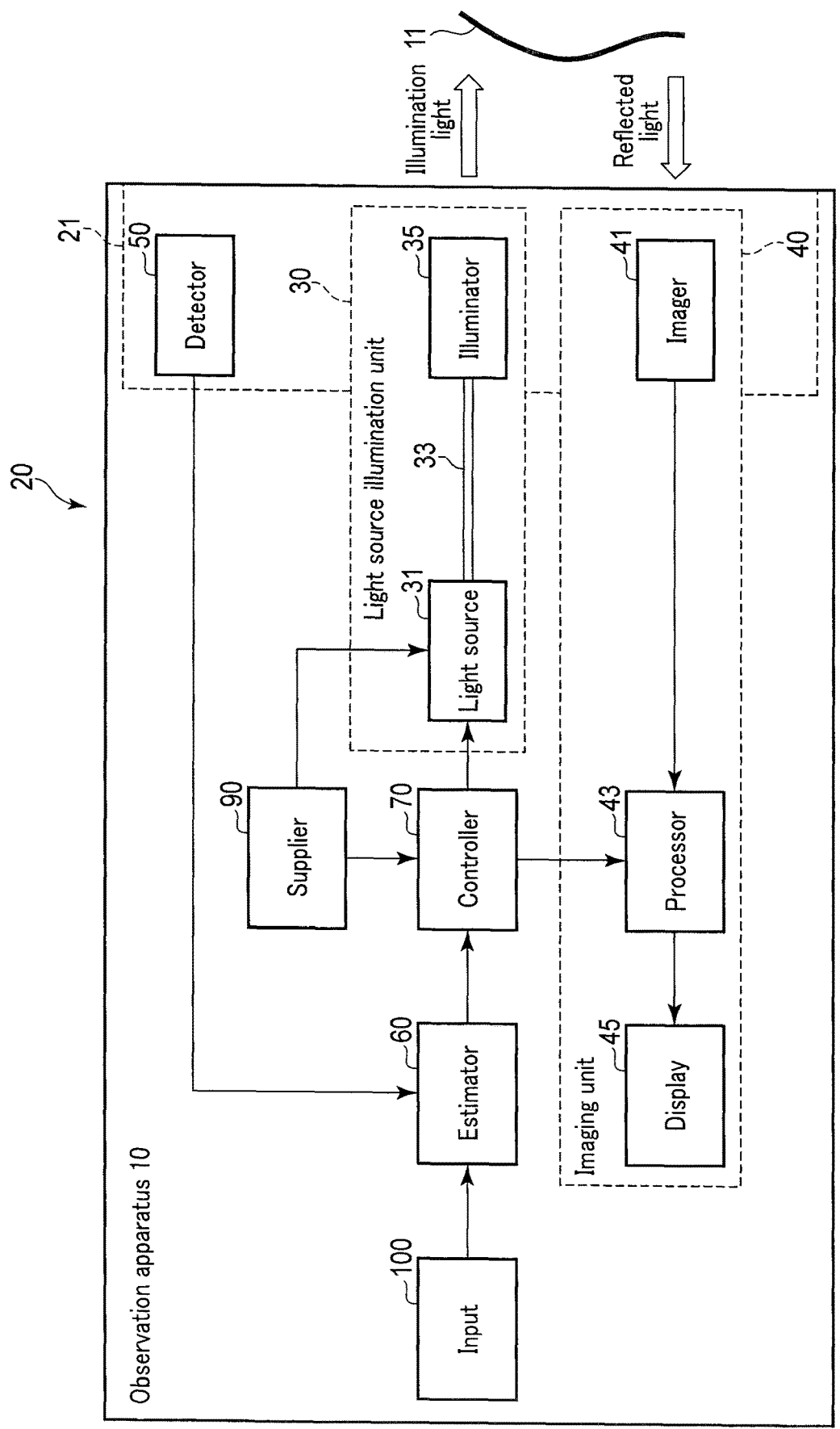
FIG. 3C is a schematic diagram of the observation apparatus according to the second embodiment having the detector.

The scheduled use time may have a time necessary to pull out the endoscope equipped with the observation apparatus 10. In this case, as shown in FIG. 3C, the observation apparatus 10 has the detector 50 which is provided in the part 21 where the illuminator 35 of the light source illumination unit 30 that illuminates illumination light to the observation target 11 is provided and which detects the position information for the part 21. For example, the detector 50 is provided at the distal end of the insertion portion of the endoscope. The detector 50 detects the position of the distal end relative to the observation target 11, and detects which observation part of the observation target 11 is detected. The estimator 60 estimates the scheduled use time information on the basis of the position information. In this case, a data table indicating the relation between the observation part in the observation target 11 and a pull-out time corresponding to this observation part is previously stored in the unshown storage. For example, the estimator 60 may estimate, on the basis of the position information and the data table, the pull-out time before the insertion portion is pulled out from this observation part to, for example, the outside of the body, and determine this time as the scheduled use time information.

The detector 50 detects a state of the shift from the first usage to the second usage or a state of the shift from the second usage to the first usage during the pull-out of the insertion portion or before the insertion portion reaches the observation target 11. In this instance, the controller 70 may select the intermediate electric power mode for the light source illumination unit 30 in the third usage and the transition state on the basis of the detection result by the detector 50.

Although the controller selects one of the operation modes in the above, the controller does not need to be limited to this. For example, the controller may select at least one of the operation modes or select a combination of the operation modes in accordance with the scheduled usage.

The supplier 90 may supply electric power to the imaging unit 40 and other parts. The controller 70 has the electric power consumption information for destinations of the electric power supply such as the imaging unit 40, and may calculate the usable time information on the basis of such electric power consumption information and the electric power consumption information for the light source 31.

[First Modification]

As shown in FIG. 4A, more than one light source illumination unit 30 are provided. The optical characteristics of the light source illumination units 30 may be the same or different from one another. The number of the light source illumination units 30 is not specifically limited.

The number of the light sources 31 does not need to be the same as the number of the illuminators 35, and does not need to be limited to this. More than one light source 31 may operate so that illumination lights having various optical characteristics may be emitted from one illuminator 35. In this case, the illumination light may be light in which lights of many colors generated from lasers and LEDs are coupled. The light source 31 may have a function which enables the switch of colors and the adjustment of colors. The observation apparatus 10 may be configured to divide the light from the light source 31 and emit the light from more than one illuminator 35.

In the above, the light source illumination units 30 may illuminate more than one kind of illumination light different in wavelength spectrum. The controller 70 may control the light source 31 so that first illumination light may be illuminated in the normal electric power mode, and second illumination light may be illuminated with electric power consumption lower than electric power consumption for the use of the first illumination light in the low electric power mode.

Figure 4B:
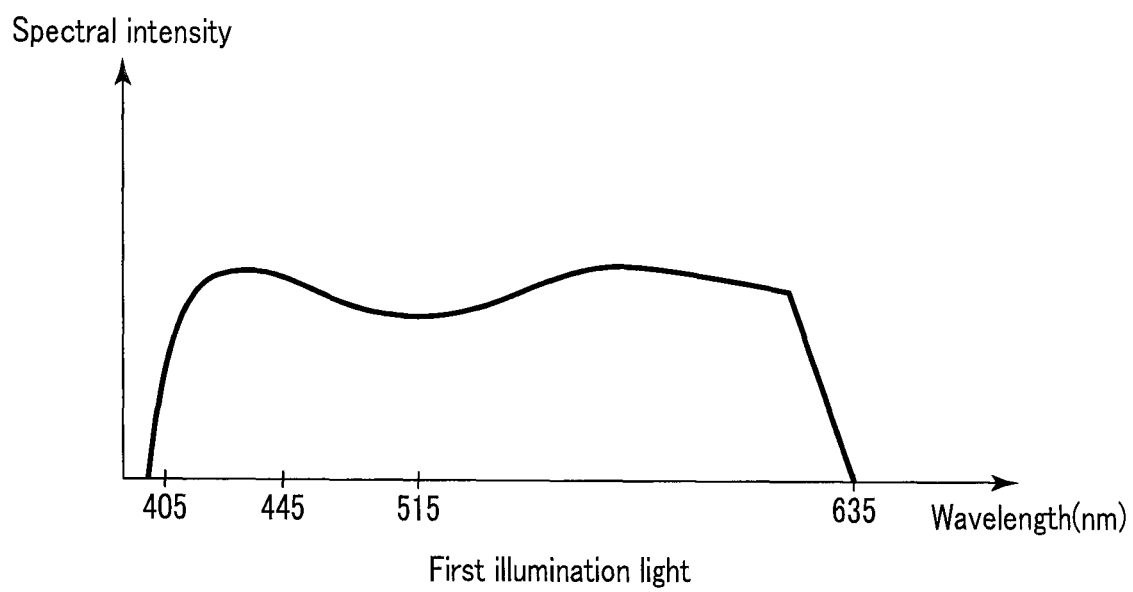
FIG. 4B is a graph showing the spectral intensity of first illumination light.

As shown in FIG. 4B, for example, the first illumination light is white light.

Figure 4C:
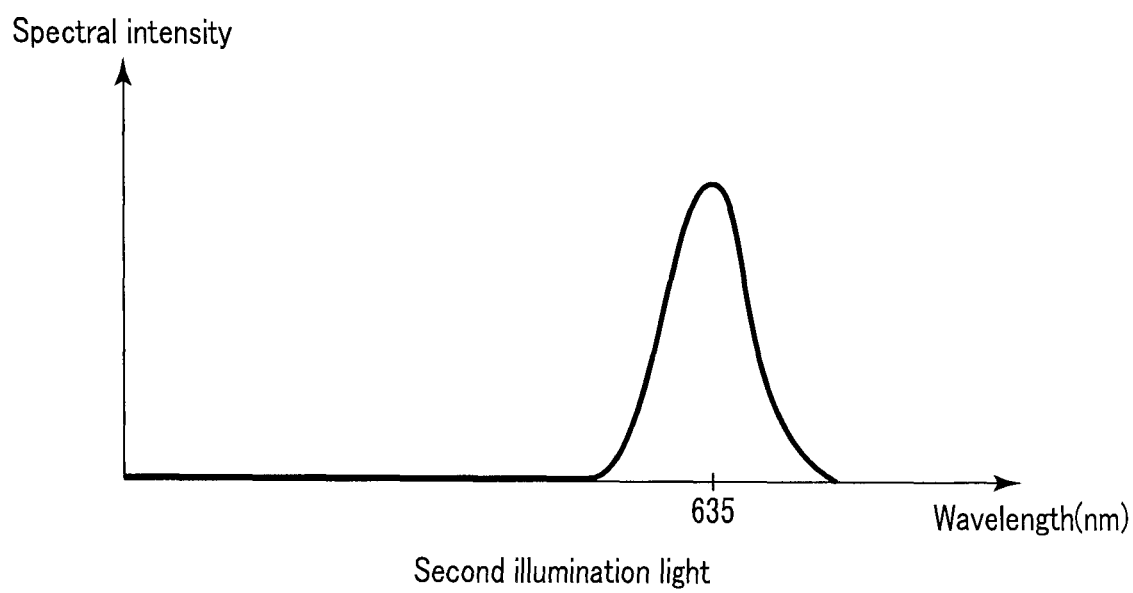
FIG. 4C is a graph showing the spectral intensity of second illumination light.
Figure 4D:
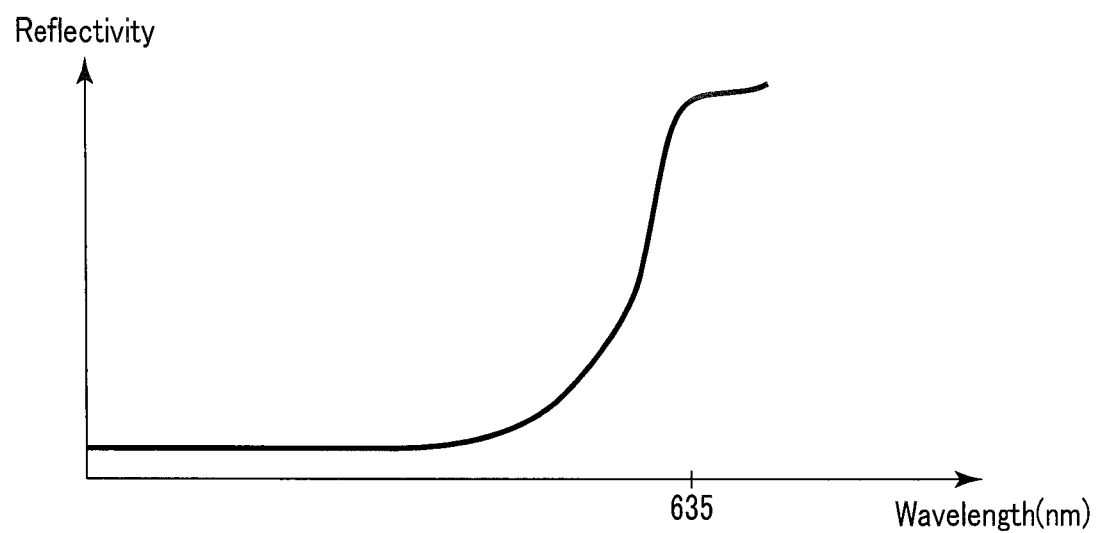
FIG. 4D is a graph showing the reflectivity of an observation target.

The spectrum of the second illumination light is decided on the basis of the reflection spectral characteristics of the observation target 11. For example, when the observation target 11 has a reflection spectrum that reflects red-range light more than in other wavelength ranges as shown in FIG. 4D, the second illumination light has more light intensity in the red range than the first illumination light, and does not have any intensity in other wavelength ranges, as shown in FIG. 4C. Thus, the second illumination light has more light in a wavelength range belonging to wavelength ranges in which the reflectivity of the observation target 11 is high than the first illumination light.

Thus, if the observation target 11 is illuminated by the second illumination light resulting from the same electric power consumption as the first illumination light, a greater reflected light amount is obtained than by the first illumination light. Therefore, in the low electric power mode, the same reflected light amount as that in the normal electric power mode can be obtained even by the second illumination light resulting from the electric power consumption less than that in the normal electric power mode.

The spectrum of the light source 31 is decided on the basis of the reflection spectral characteristics of the observation target 11 as described above, but does not need to be limited to this. The spectrum of the light source 31 may be decided on the basis of the sensitivity characteristics of the imager 41. For example, when the low electric power mode and the normal electric power mode are driven with the same electric power consumption, the second illumination light has more light in a wavelength range belonging to wavelength ranges in which the sensitivity of the imager 41 is high than the first illumination light, and does not have any intensity in other wavelength ranges.

In the present modification, when the observation target 11 has specific spectral characteristics of a living body or the like, information on the observation target 11 can be efficiently taken out, and electric power consumption can be reduced.

The second illumination light has the wavelength spectrum having components in the red range alone in the above explanation, but does not need to be limited to this. The second illumination light may have, for example, a wavelength spectrum at a higher rate in the red range and at a lower rate in other ranges. In this case, regarding each of colors separated by the imager 41 to acquire an image, the amplification factor of each color of the imager 41 should be set so that an image shows white when the second illumination light is illuminated to the white observation target 11.

The light source illumination units 30 may be configured so that the first illumination light is white light high in color rendering, and the second illumination light will be white light which is low in color rendering but which is highly efficient.

The second illumination light may have a narrower distribution than the first illumination light but can be emitted with lower electric power consumption.

The present application permits a suitable combination of each of the embodiments and each of the modifications, such as a combination of the first embodiment and the modification of the second embodiment.

The present invention is not completely limited to the embodiments described above, and modifications of components can be made at the stage of carrying out the invention without departing from the spirit thereof. Further, various inventions can be made by properly combining the components disclosed in the embodiments described above.

What is claimed is:

1. An observation apparatus comprising:
a light source illumination unit comprising an illuminator configured to emit illumination light to an observation target, wherein the light source illumination unit is configured to operate in operation modes comprising a normal electric power mode to operate with first electric power consumption and a low electric power mode to operate with second electric power consumption lower than the first electric power consumption;
an endoscope comprising an elongated insertion portion, wherein a distal end of the insertion portion is configured to be inserted into a subject including the observation target while a proximal end of the insertion portion remains outside of the subject;
an imaging unit configured to image the observation target by receiving light reflected by the observation target to which the illumination light is emitted;
a first detector provided at the distal end of the insertion portion of the endoscope, wherein the first detector is configured to detect at least one piece of information including motion information for the distal end of the insertion portion of the endoscope and position information for a position change amount of the distal end of the insertion portion of the endoscope;

an estimator configured to estimate whether a current usage of the observation apparatus is a first usage or a second usage based on the at least one piece of information obtained from the first detector, wherein necessity of operating the light source illumination unit in the first usage is greater than in the second usage; and a controller configured to:
select the normal electric power mode from among the operation modes in the first usage and the low electric power mode from among the operation modes in the second usage, on the basis of the current usage estimated by the estimator; and control the light source illumination unit in accordance with a selected one of the normal electric power mode and the low electric power mode.

2. The observation apparatus according to claim 1, further comprising a second detector configured to detect whether the observation apparatus is grasped by an observer,
wherein when the second detector detects that the observation apparatus is grasped, the estimator is configured to estimate that the current usage for observation is the first usage, and
wherein when the second detector detects that the observation apparatus is not touched, the estimator is configured to estimate that the current usage is the second usage.

3. The observation apparatus according to claim 1,
wherein the imaging unit comprises:
an imager configured to image the observation target;
a processor configured to process an imaging signal output from the imager into a desired state; and
a display configured to display an image on the basis of the imaging signal processed by the processor,
wherein the observation apparatus further comprises a third detector configured to detect a state of an electric power supply of the processor and a state of an electric power supply of the display,
wherein when the third detector detects that both the electric power supplies of the processor and the display are on, the estimator is configured to estimate that the current usage is the first usage, and
wherein when the third detector detects that the electric power supply of the processor or the electric power supply of the display is off, the estimator estimates that the current usage is the second usage.

4. The observation apparatus according to claim 1,
wherein the imaging unit comprises:
an imager configured to image the observation target; and
a transmission path to transmit an imaging signal output from the imager,
wherein the observation apparatus further comprises a fourth detector configured to detect a connection state of the transmission path,
wherein when the fourth detector detects that the connection state of the transmission path is connected, the estimator is configured to estimate that the current usage is the first usage, and
wherein when the fourth detector detects that the connection state of the transmission path is disconnected, the estimator is configured to estimate that the current usage is the second usage.

5. The observation apparatus according to claim 1,
wherein the operation modes further comprise an intermediate electric power mode to operate with third electric power consumption lower than the first electric power consumption and higher than the second electric power consumption,
wherein the estimator is configured to estimate a third usage in which necessity of operating the light source illumination unit is smaller than in the first usage and greater than in the second usage, and a transition state of transition from the first usage to the second usage or from the second usage to the first usage, and
wherein the controller is configured to select the intermediate electric power mode from among the operation modes in the third usage and the transition state.

6. The observation apparatus according to claim 1,
wherein in the case where the operation mode of the light source illumination unit is the low electric power mode, the controller is configured to control the light source illumination unit and the imaging unit so that a luminance of an imaging signal output from the imaging unit in the low electric power mode is kept at a luminance of an imaging signal output from the imaging unit in the normal electric power mode, even when the electric power consumption of the light source illumination unit is the second electric power consumption.

7. The observation apparatus according to claim 6,
wherein in the case where the operation mode of the light source illumination unit is the low electric power mode, the controller is configured to control the light source illumination unit and the imaging unit so that a frame rate of an imager of the imaging unit in the low electric power mode is lower than a frame rate of the imager in the normal electric power mode and the light source illumination unit emits illumination light in a period of exposure of the imager.

8. The observation apparatus according to claim 6,
wherein the imaging unit comprises an imager configured to image the observation target, and
wherein when the operation mode of the light source illumination unit is the low electric power mode, the controller is configured to control the light source illumination unit and the imaging unit so that an imaging gain for the imaging signal of the imager in the low electric power mode is greater than an imaging gain for the imaging signal of the imager in the normal electric power mode and the illumination light amount of the light source illumination unit in the low electric power mode is smaller than the illumination light amount of the light source illumination unit in the normal electric power mode.

9. The observation apparatus according to claim 1,
wherein the light source illumination unit is configured to emit more than one kind of illumination light different in wavelength spectrum, and
wherein the controller is configured to control the light source illumination unit so that first illumination light is emitted in the normal electric power mode, and second illumination light is emitted with electric power consumption lower than electric power consumption for the use of the first illumination light in the low electric power mode.

10. The observation apparatus according to claim 9,
wherein the second illumination light has more light in a wavelength range belonging to wavelength ranges in which a reflectivity of the observation target is high than the first illumination light.

11. The observation apparatus according to claim 9,
wherein the imaging unit comprises an imager configured to image the observation target, and
wherein the second illumination light has more light in a wavelength range belonging to wavelength ranges in which a sensitivity of the imager is high than the first illumination light.

12. The observation apparatus according to claim 10,
wherein the imaging unit comprises an imager configured to image the observation target, and
wherein regarding each of colors separated by the imager to acquire an image, an amplification factor of each color of the imager is set so that an image shows white when the second illumination light is applied to a white observation target.

13. The observation apparatus according to claim 1,
wherein the light source illumination unit comprises:
  a laser light source configured to emit laser light;
  a light guide configured to guide the laser light emitted from the laser light source; and
  the illuminator comprising a wavelength converting member configured to absorb the laser light guided by the light guide, convert some of the laser light that is absorbed to converted light, and then emit the converted light to an outside.

14. An endoscope system comprising the observation apparatus according to claim 1.

15. An observation apparatus comprising:
a light source illumination unit comprising an illuminator configured to emit illumination light to an observation target, wherein the light source illumination unit is configured to operate in operation modes comprising a normal electric power mode to operate with first electric power consumption and a low electric power mode to operate with second electric power consumption lower than the first electric power consumption;
an imaging unit configured to image the observation target by receiving light reflected by the observation target to which the illumination light is emitted;
a first detector provided in a part where the illuminator is provided, wherein the first detector is configured to detect at least one piece of information including motion information for the part and position information for a position change amount of the part;
an estimator configured to estimate whether a current usage of the observation apparatus is a first usage or a second usage based on the at least one piece of information obtained from the first detector, wherein necessity of operating the light source illumination unit in the first usage is greater than in the second usage; and
a controller configured to:
  select the normal electric power mode from among the operation modes in the first usage and the low electric power mode from among the operation modes in the second usage, on the basis of the current usage estimated by the estimator; and
  control the light source illumination unit in accordance with a selected one of the normal electric power mode and the low electric power mode,
wherein the first detector comprises one of: an acceleration sensor, an angular velocity sensor, a global positioning system (GPS) sensor, a wireless strength-based positioning sensor, and a geomagnetic sensor.

16. The observation apparatus according to claim 15, further comprising a second detector configured to detect whether the observation apparatus is grasped by an observer,
wherein when the second detector detects that the observation apparatus is grasped, the estimator is configured to estimate that the current usage for observation is the first usage, and
wherein when the second detector detects that the observation apparatus is not touched, the estimator is configured to estimate that the current usage is the second usage.

17. The observation apparatus according to claim 15,
wherein the imaging unit comprises:
  an imager configured to image the observation target;
  a processor configured to process an imaging signal output from the imager into a desired state; and
  a display configured to display an image on the basis of the imaging signal processed by the processor,
wherein the observation apparatus further comprises a third detector configured to detect a state of an electric power supply of the processor and a state of an electric power supply of the display,
wherein when the third detector detects that both the electric power supplies of the processor and the display are on, the estimator is configured to estimate that the current usage is the first usage, and
wherein when the third detector detects that the electric power supply of the processor or the electric power supply of the display is off, the estimator estimates that the current usage is the second usage.

18. The observation apparatus according to claim 15,
wherein the imaging unit comprises:
  an imager configured to image the observation target; and
  a transmission path to transmit an imaging signal output from the imager,
wherein the observation apparatus further comprises a fourth detector configured to detect a connection state of the transmission path,
wherein when the fourth detector detects that the connection state of the transmission path is connected, the estimator is configured to estimate that the current usage is the first usage, and
wherein when the fourth detector detects that the connection state of the transmission path is disconnected, the estimator is configured to estimate that the current usage is the second usage.

19. The observation apparatus according to claim 15,
wherein the operation modes further comprise an intermediate electric power mode to operate with third electric power consumption lower than the first electric power consumption and higher than the second electric power consumption,
wherein the estimator is configured to estimate a third usage in which necessity of operating the light source illumination unit is smaller than in the first usage and greater than in the second usage, and a transition state of transition from the first usage to the second usage or from the second usage to the first usage, and
wherein the controller is configured to select the intermediate electric power mode from among the operation modes in the third usage and the transition state.

20. The observation apparatus according to claim 15,
wherein in the case where the operation mode of the light source illumination unit is the low electric power mode, the controller is configured to control the light source illumination unit and the imaging unit so that a luminance of an imaging signal output from the imaging unit in the low electric power mode is kept at a luminance of an imaging signal output from the imaging unit in the normal electric power mode, even when the electric power consumption of the light source illumination unit is the second electric power consumption.

* * * * *